United States Patent [19]

Sakano

[11] Patent Number: 5,755,749
[45] Date of Patent: May 26, 1998

[54] CHANGE CONTROL METHOD USING THREE-DIMENSIONAL 1/F FLUCTUATION, RECORDING MEDIUM STORING THE METHOD, AND CHANGE CONTROL DEVICE USING THREE-DIMENSIONAL 1/F FLUCTUATION

[75] Inventor: Kazuhito Sakano, Funahashi-mura, Japan

[73] Assignee: Toyo Sangyo Co., Ltd., Japan

[21] Appl. No.: 690,894

[22] Filed: Aug. 1, 1996

[30] Foreign Application Priority Data

Aug. 8, 1995 [JP] Japan .................................. 7-202342

[51] Int. Cl.$^6$ .................................................. A61N 1/32
[52] U.S. Cl. ........................... 607/73; 607/39; 607/148
[58] Field of Search .......................... 607/72, 73, 46, 607/63, 74, 145, 148, 59, 142

[56] References Cited

U.S. PATENT DOCUMENTS

| | | | |
|---|---|---|---|
| 4,254,776 | 3/1981 | Tanie et al. | 607/66 |
| 4,338,945 | 7/1982 | Kosugi et al. | 607/73 |
| 4,390,023 | 6/1983 | Rise | 607/73 |
| 4,926,864 | 5/1990 | Dufresne et al. | 607/59 |
| 5,578,065 | 11/1996 | Hattori et al. | 607/46 |

FOREIGN PATENT DOCUMENTS

| | | |
|---|---|---|
| 62-137067 | 6/1987 | Japan . |
| 63-192459 | 8/1988 | Japan . |
| 63-257577 | 10/1988 | Japan . |

*Primary Examiner*—William E. Kamm
*Assistant Examiner*—Carl H. Layno
*Attorney, Agent, or Firm*—Michaelson & Wallace; Peter L. Michaelson; John T. Peoples

[57] ABSTRACT

A method for controlling changes in stimulation of every sort and kind including electrical stimulation, utilizes a three-dimensional 1/f fluctuation. The method is a change control method for controlling changes in stimulation to an object using a three-dimensional 1/f fluctuation and includes the steps of causing changes based upon 1/f fluctuation periods in the X-Z plane of a X-Y-Z space, causing changes based upon 1/f fluctuation periods in the X-Y plane of the space, superposing the caused changes of the previous steps, and applying the superposed caused changes to the object. This makes it possible to realize a low-frequency device free of problems attributable to the tolerance in neural response. A recording medium used to store the change control method, and a change control device using a three-dimensional 1/f fluctuation are also disclosed. Changes based on 1/f fluctuation periods in the X-Z plane and changes based on 1/f fluctuation periods in the X-Y plane are superposed on each other. In the case where stimulation is changed so as to avoid monotonous application of stimulation, for example, in a massaging device, it is possible to perform control for providing three-dimensional changes in the stimulation in which changes occur in both the vertical and horizontal directions, in addition to changes in the stimulation based on two-dimensional 1/f fluctuation periods at a single stimulation point. Thus, it becomes possible to effect control for stimulation changes which are natural and comfortable to an extent that they are closely correspond to the human physiology.

19 Claims, 14 Drawing Sheets

CHANGE CONTROL METHOD USING THREE-DIMENSIONAL 1/F FLUCTUATION, RECORDING MEDIUM STORING THE METHOD, AND CHANGE CONTROL DEVICE USING THREE-DIMENSIONAL 1/F FLUCTUATION

BACKGROUND OF THE INVENTION

1. Field of the Invention

The present invention relates to a change control method using a three-dimensional 1/f fluctuation for controlling changes in stimulation of every sort and kind including electrical stimulation, a recording medium in which the method is stored, and a change control device using a three-dimensional 1/f fluctuation.

2. Description of the Related Art

As a pattern of changes in stimulation, including electrical stimulation, those utilizing 1/f fluctuation have been proposed in, for example, scientific literatures. 1/f fluctuation is found, for example, in classical music pieces, the rhythm of jazz and rock music, and even in a comfortable breeze and the sound of the sea waves at the water's edge. Also, with regard to the human body, it is known that brain waves ($\alpha$ waves) during the state of meditation and the heart beat period at rest both involve 1/f fluctuation. The 1/f fluctuation itself is known to give peace of mind or a sense of relief to a person.

Experiments using such 1/f fluctuation in a massaging machine, as well as the results of their evaluations on comfortableness, have been reported in literatures, etc. When the theory of 1/f fluctuation is applied to a low-frequency electrotherapeutic device, there are obtained such stimulation changes with elapse of time, as shown in FIG. 11. Also shown in FIG. 11, the stimulation has fluctuation periods T1, T2, T3,T4, T5, etc., so that the stimulation exhibits a 1/f fluctuation in two dimensions along the X and Z axes. Based on the theory of 1/f fluctuation, such a two-dimensional 1/f fluctuation can be obtained by changing the strength of stimulation or the height of the waveform of an output voltage from a different electrode, as well as the period of the waveform.

Even if the 1/f fluctuation theory is applied to a conventional low-frequency electrotherapeutic device a satisfactory effect cannot be obtained, because the conventional low-frequency electrotherapeutic device generally has only a different electrode and an indifferent electrode disposed in a pair to be used as therapeutic electrodes. Exceptionally, in Japanese Patent Application Laid-Open No. 63-192459, there is proposed a low-frequency electrotherapeutic device wherein five pairs are provided, each pair comprising a dot-like positive electrode 101 and an annular negative electrode 102, as shown in FIG.12. In this low-frequency electrotherapeutic device, although five pairs of different electrodes and indifferent electrodes are arranged in a rectangular shape, the structure thereof can be regarded as essentially using only a single pair comprising a different electrode and an indifferent electrode. In Japanese Patent Application Laid-Open No. 63-257577, there is proposed a low-frequency electrotherapeutic device having a different electrode 103 and an indifferent electrode 104 which are concentric with each other, as shown in FIG. 13. The structure of this low-frequency electrotherapeutic device also be regarded as including only a pair comprising a different electrode and an indifferent electrode. Further, in Japanese Patent Application Laid-Open No. 62-137067 is proposed a low-frequency electrotherapeutic device wherein three electrodes are arranged in parallel, with the central electrode being used as an indifferent electrode while the electrodes located at either side of the central electrode are used as different electrodes which are simultaneously supplied with an electric current. However, even in the low-frequency electrotherapeutic device described in Japanese Patent Application Laid-Open No. 62-137067, the two different electrodes are electrified simultaneously; hence the structure of the device can also be regarded as essentially using a single pair comprising a different electrode and an indifferent electrode.

Thus, each of the conventional low-frequency electrotherapeutic devices referred to above consists essentially of a single pair comprising a different electrode and an indifferent electrode, wherein the positional relationship between the different electrode and the indifferent electrode is fixed. An electrical circuit, through which a stimulating current flows from the positive electrode to the negative electrode, is always formed at a limited position of the skin of a living body; that is, stimulation is repeated at the same position adjoining the skin of the living body. Further, even if the 1/f fluctuation theory is applied to a conventional electrotherapeutic device, stimulation is merely changed at a fixed position of a living body. Even if stimulation having 1/f fluctuation and therefore having a certain strength and rhythm is repeatedly applied, the repetitive application is performed at the fixed position. Continuing an electrical stimulation at such a fixed position on the skin of a living body is uncomfortable to the living body even if the stimulation has 1/f fluctuation. And continuing the electric stimulation at such a limited position on the living body skin makes the stimulation less effective due to habituation.

The above-described problems in relation to the stimulating current being applied at the same position of the body occur even in the structure wherein a different electrode and an indifferent electrode are connected through lead wires to a controller so as to allow the distance between both electrodes on a living body to be freely changed, or even in the structure having five pairs, each pair comprising a different electrode and an indifferent electrode, such as that shown in FIG. 12, because once the different electrode(s) and the indifferent electrode(s) are attached to a living body, their positional relation becomes fixed. Therefore, the foregoing problems have been solved by neither the low-frequency electrotherapeutic devices presently available in the market nor those proposed in the past.

In efforts to solve the above-mentioned problem, there have heretofore been conducted studies regarding the method of varying the voltage waveform outputted from a different electrode so as to thereby automatically change the type of stimulation in the range of at least three patterns and at most seven or eight patterns, as shown in FIGS. 14 and 15.

However, even if the width and magnitude of each pulse in the pattern are changed shown in FIG. 14, or the stimulation pattern is changed as in FIG. 15, the human becomes less sensitive to such stimulating current. That is, any person, in his or her neural response, exhibits a tolerance against stimulation repeated at the same position on his or her body. As a result, no matter how the type of stimulation may be changed, the person loses sensitivity in discriminating between stimulation with respect to the type and strength. This phenomenon is well known within the field of physiology. Consequently, even with stimulation pattern changed as in FIG. 15, for example, even if a weak stimulation is given to a human just after a strong stimulation (such as voltage V2 after V1 or voltage V4 after V3 in FIG. 14), the human can no longer sense it as stimulation. The longer continued the stimulation, the more marked this tendency.

Thus, according to the electrode structure of the conventional low-frequency electrotherapeutic devices wherein the positional relationship between a different electrode and an indifferent electrode is fixed, a patient being treated by the device exhibits a tolerance in his or her neural response, with the result that the effects of treatment for diseases of the nervous system such as neuralgia and palsy of the peripheral nerve, which treatment effects are clearly mentioned to be provided by the electrotherapeutic devices, become deteriorated with the lapse of working time of the devices.

In addition to the above problem relating to the tolerance in neural response, there also has been the problem that an electric charge is accumulated in the human living body tissue due to the electric current outputted from the low-frequency electrotherapeutic devices. More particularly, as long as the positional relation between the different electrode and the indifferent electrode within each such low-frequency electrotherapeutic device remains fixed, the path of electric current also becomes fixed and the aforesaid accumulation of electric charge in the living body also occurs at the same position. As a result, the waveform of the output voltage from the different electrode is greatly distorted; therefore, a stimulating electric current has difficulty in flowing through the living body and the patient undergoing medical treatment feels stimulation only to an extremely slight degree.

Due to the aforesaid accumulation of electric charge in the living body caused by continued stimulation at the same position of the living body, effects of massage such as the recovery from fatigue and the promotion of blood circulation are also deteriorated.

Even apart from the problems caused by the tolerance in neural response and the problems caused by accumulation of electric charge in the living body, the repeated electric stimulation at the same position of the living body causes discomfort.

The fundamental problem encountered in the conventional low-frequency electrotherapeutic devices is difficulty in controlling changes in stimulation applied to a living body.

SUMMARY OF THE INVENTION

The present invention has been accomplished in view of the above-mentioned problem of the prior art technique, and it is an object of the invention to provide a change control method using a three-dimensional 1/f fluctuation such as in an electrical stimulation which solves the problems caused by tolerance in neural response as well as those caused by accumulation of electric charge in a living body, thereby attaining a comfortable massaging effect and which is applicable, for example, to a low-frequency electrotherapeutic device. The present invention also provides a recording medium in which the said method is stored, and a change control device using 1/f fluctuation.

In order to achieve the above-mentioned object, the present invention provides a change control method for controlling changes in stimulation to an object using a three-dimensional 1/f fluctuation includes the steps of causing changes based upon 1/f fluctuation periods in the X-Z plane of a X-Y-Z space, causing changes based upon 1/f fluctuation periods in the X-Y plane of the space, superposing the caused changes of the previous steps, and applying the superposed caused changes to the object.

The present invention also provides a recording medium read out by a computer which a stores a change control method using a three-dimensional 1/f fluctuation, the medium being characterized in that changes based on 1/f fluctuation periods in the X-Z plane within an X-Y-Z space and changes based on 1/f fluctuation periods in the X-Y plane within the space are superposed on each other.

This invention is applied to provide a low-frequency electrotherapeutic device that solves the problems caused by tolerance in neural response as well as those caused by accumulation of electric charge in a living body, thereby attaining a comfortable massaging effect.

Examples of the "recording medium" as referred to herein include floppy disks and memory ICs such as ROMs and RAMs which store computer software.

In the change control method using a three-dimensional 1/f fluctuation and the recording medium storing the same method according to the present invention, changes may be changes provided by mechanical motions.

Examples of the "mechanical motions" as referred to herein include massaging motions, such as "kneading", "rubbing","and "tapping" for a living body, which are obtained by mechanical application of forces in a massaging device.

Examples of the "changes in stimulation" as referred to herein include changes in optical stimulation detectable to the sense of sight, changes in mechanical friction detectable to the sense of touch, changes in thermal stimulation, changes in stimulation caused by vibration, and changes in stimulation caused by pneumatic waves detectable to the sense of hearing.

An example of "electrical stimulation" as referred to herein is electrical stimulation created by a low-frequency electrotherapeutic device.

By the application of the change control method using a three-dimensional 1/f fluctuation according to the present invention, it is possible to design changes of topographical undulations formed artificially such as those in parks, golf courses, and ski areas and it is also possible to draw up an overall city plan.

More particularly, it is possible to design changes of undulations in artificial formations such as plastic images, monuments, buildings and roller coasters installed in amusement parks.

For example, by the application of the change control method using a three-dimensional 1/f fluctuation according to the present invention, it is possible to control changes in wave motions of a fluid; e.g. water, in an amusement facility such as a "wavy pool." It is also possible to control changes of wavy motions created in a fluid stored in a piece of furniture; e.g. a glass tank, which is disposed for ornamental purposes.

The use of a three-dimensional 1/f fluctuation enables control of changes in artificial creation of wind pressure, sound pressure, or water pressure.

The present invention also provides a change control device using a three-dimensional 1/f fluctuation. The change control device has a change control means for creating changes within an X-Y-Z space, wherein changes in the X-Z plane created based on 1/f fluctuation periods and changes in the X-Y plane created based on 1/f fluctuation periods are superposed on each other.

The present invention further provides a change control method using a three-dimensional 1/f fluctuation, wherein three or more electrodes provided in an X-Y-Z space are used. The strength of stimulation provided by each electrode (namely, the height of the waveform of an output voltage from a exploring electrode) is changed with time in accordance with a 1/f fluctuation; and further, the timing of designating each electrode as a different or an indifferent electrode is changed in accordance with a 1/f fluctuation.

The present invention provides a change control device using a three-dimensional fluctuation, which comprises a step-up pulse circuit, a control section (CPU) for controlling the step-up pulse circuit, a power source for the supply of electric power to both the step-up pulse circuit and the control section (CPU), an output circuit connected to the step-up pulse circuit and which is controlled by the control section (CPU), and electrodes connected to the output circuit. In the change control device, three or more electrodes are provided in an X-Y-Z space, and changes of stimulation based on 1/f fluctuation periods in the X-Z plane created by the electrodes and changes of stimulation based on 1/f fluctuation periods in the X-Y plane created by the electrodes are superposed on each other.

The present invention also provides a change control device using a three-dimensional 1/f fluctuation which comprises a step-up pulse circuit, a control section (CPU) for controlling the step-up pulse circuit, a power source for the supply of electric power to both the step-up pulse circuit and the control section (CPU), an output X circuit connected to the step-up pulse circuit and which is controlled by the control section (CPU), and electrodes connected to the output circuit. In the change control device, three or more electrodes are provided in an X-Y-Z space. The strength of stimulation provided by each electrode (namely, the height of the waveform of an output voltage from a different electrode) is changed with time in accordance with a 1/f fluctuation; and further, the timing of designating each electrode as a different or an indifferent electrode is changed in accordance with a 1/f fluctuation.

The change control method using a three-dimensional 1/f fluctuation according to the present invention is applicable to a low-frequency therapeutic process as a low-frequency electrotherapeutic method, and the change control device using a three-dimensional 1/f fluctuation according to the present invention can be constituted as a low-frequency electrotherapeutic device. Further, the recording medium which stores the change control method using a three-dimensional 1/f fluctuation according to the present invention can be constituted as, for example, a magnetic card, a floppy disk, or a compact disk, for installing a control program into a low-frequency electrotherapeutic device which is controlled with a computer.

However, the change control method using a three-dimensional 1/f fluctuation and the change control device using the same fluctuation, both according to the present invention, are not limited to a low-frequency electrotherapeutic method and a low-frequency electrotherapeutic device. For example, the said change control method can be applied to designing changes of undulation in parks, golf courses, and ski areas. It is also applicable to drawing up an overall city plan.

In the change control method using a three-dimensional 1/f fluctuation according to the present invention, changes based on 1/f fluctuation periods in the X-Z plane within the X-Y-Z space and changes based on 1/f fluctuation periods in the X-Y plane are superposed on each other, and, for example, in the case where changes of stimulation in the X-Y-Z space are to be controlled, vertical stimulation changes in the X-Z plane are induced on the basis of 1/f fluctuation. Subsequently, while the vertical stimulation is allowed to continue, the stimulating direction is shifted to the horizontal direction in the X-Y plane, which shift is performed on the basis of 1/f fluctuation. By so doing, it becomes possible to make a change control using a three-dimensional 1/f fluctuation wherein changes based on 1/f fluctuation periods in the X-Z plane and changes based on 1/f fluctuation periods in the X-Y plane are superposed on each other. As a result, in the case where stimulation is changed so as to avoid monotonous application of stimulation, for example, in a massaging device, not only are stimulation changes based on two-dimensional 1/f fluctuation periods made at merely a single stimulation point, but it also is possible to effect a control for obtaining three-dimensional stimulation changes spread in both vertical and horizontal directions. Thus, it becomes possible to effect control for stimulation changes which are natural and comfortable to an extent that they closely correspond to the human physiology. The present invention is applicable to massaging devices using mechanical stimulation and using electrical stimulation, etc.

BRIEF DESCRIPTION OF THE DRAWINGS

The invention will be more readily understood by reference to the following detailed description taken in conjunction with the accompanying drawings wherein.

DETAILED DESCRIPTION OF THE INVENTION

A low-frequency electrotherapeutic device, which is a change control device using a three-dimensional 1/f fluctuation according to an embodiment of the present invention, will now be described with reference to the accompanying drawings.

Figure 1A:
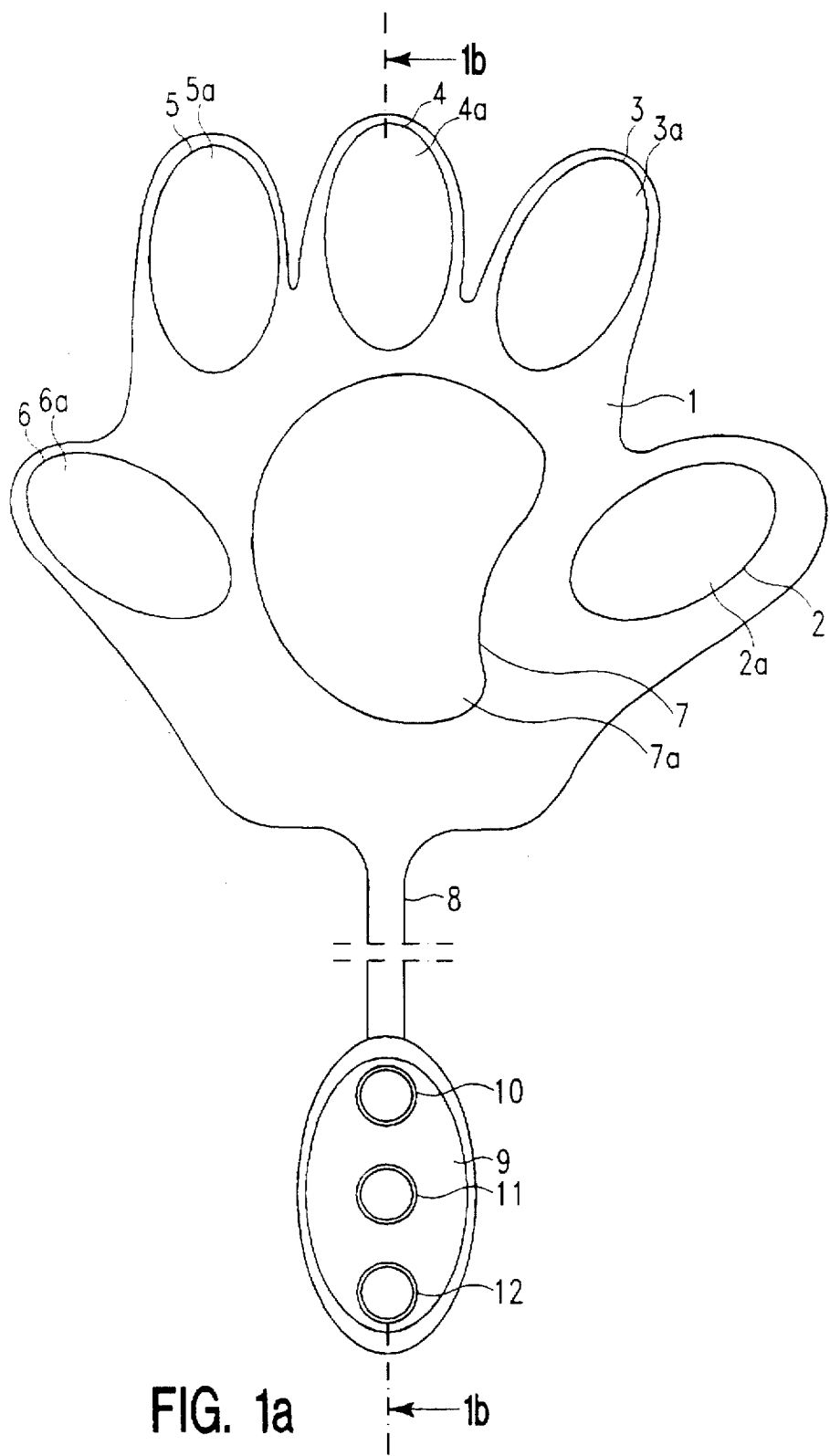
FIG.1(a) is a surface view of a low-frequency electrotherapeutic device, which is a change control device using a three-dimensional 1/f fluctuation according to an embodiment of the present invention.
Figure 1B:
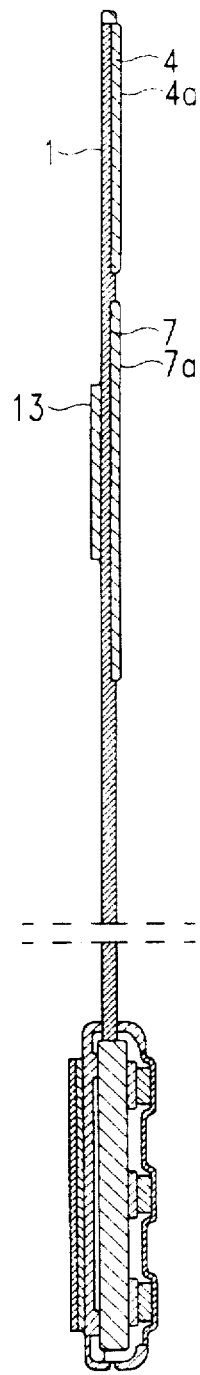
FIG.1(b) is a sectional view taken along line 1b in FIG. 1(a)

FIG. 1(a) is a surface view of a low-frequency electrotherapeutic device according to an embodiment of the present invention, showing a portion corresponding to the palm of the hand, and FIG. 1(b) is a sectional view taken along line 1b in FIG. 1(a).

In FIG. 1, reference numeral 1 denotes a base film sheet of the device body, which sheet is, for example, a vinyl chloride sheet. Electrodes 2, 3, 4, 5 and 6 have medicinal adhesive pads 2a, 3a, 4a, 5a and 6a, respectively, and are arranged non-linearly on the surface a of the base film sheet 1. In other words, the electrodes 2, 3, 4, 5 and 6 are arranged along a curved line having a curvature smaller than infinity.

In FIGS. 1(a) and 1(b), numeral 7 denotes a central electrode having a medicinal adhesive pad 7a, the central electrode 7 being disposed nearly centrally of the base film sheet 1.

One end of a pendant cable 8 is attached to the base film sheet 1, and to the opposite end thereof is connected a pendant type controller 9. The pendant type controller 9 is provided with operating buttons 10, 11 and 12. The pendant type controller 9 is attached to an extended end portion of the base film sheet 1, and the base film sheet 1 is inserted into the central portion of the controller. Among the operating buttons 10, 11 and 12, the operating buttons 10 and 12 are used for setting the voltage high or low, while the operating button 11 is used to select the type of stimulation induced by a low frequency pluses, that is, to perform mode selection.

Figure 2A:
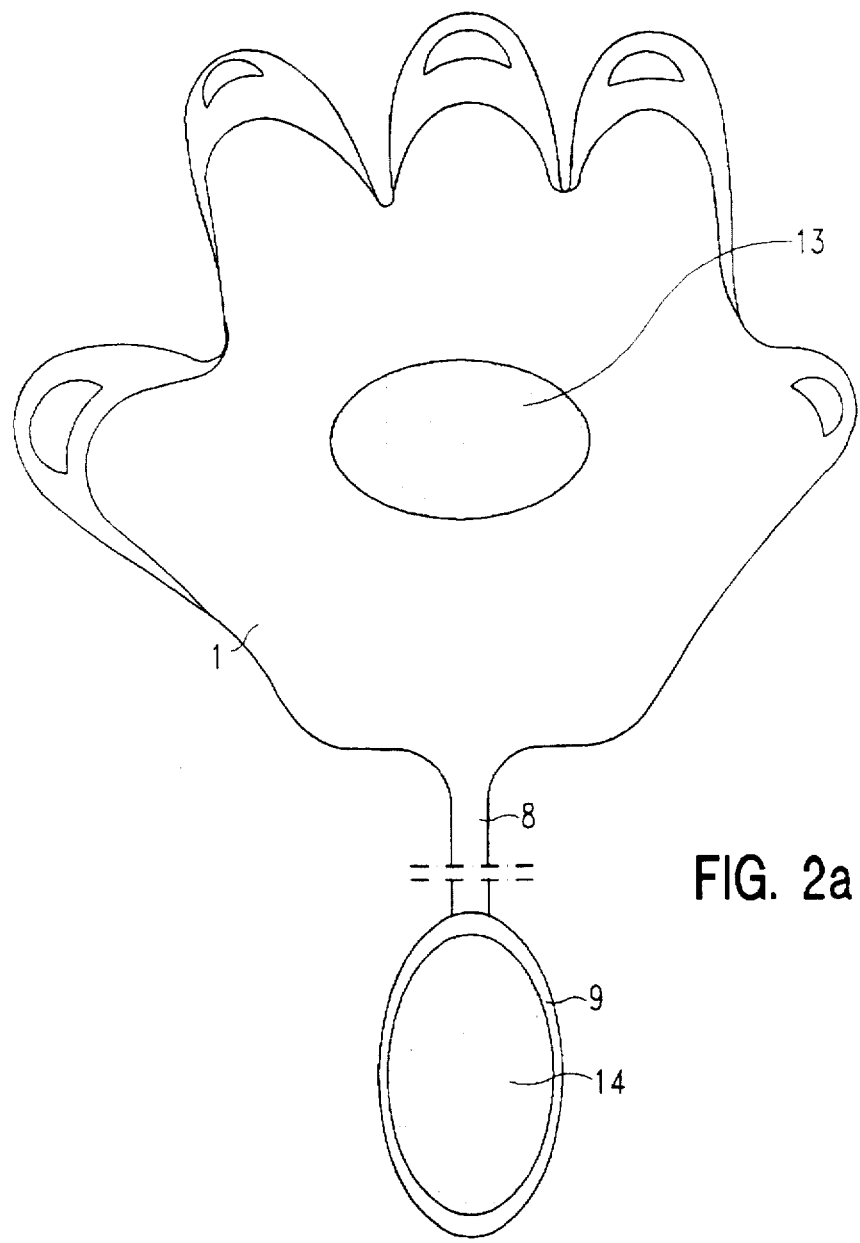
FIG.2(a) is a back view of the low-frequency electrotherapeutic device of the embodiment illustrated in FIG. 1.
Figure 2B:
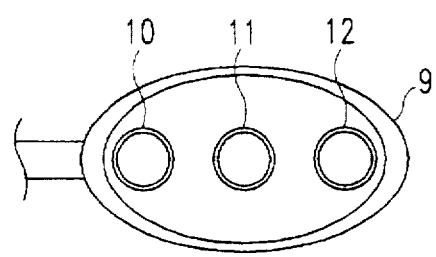
FIG.2(b) is a view as seen in the direction of arrow B in FIG. 1(a)
Figure 2C:
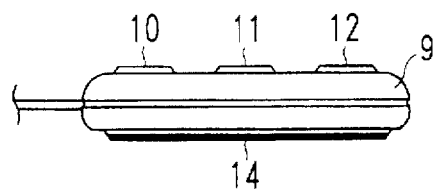
FIG. 2(c) is a side view of FIG. 2(b)
Figure 3A:
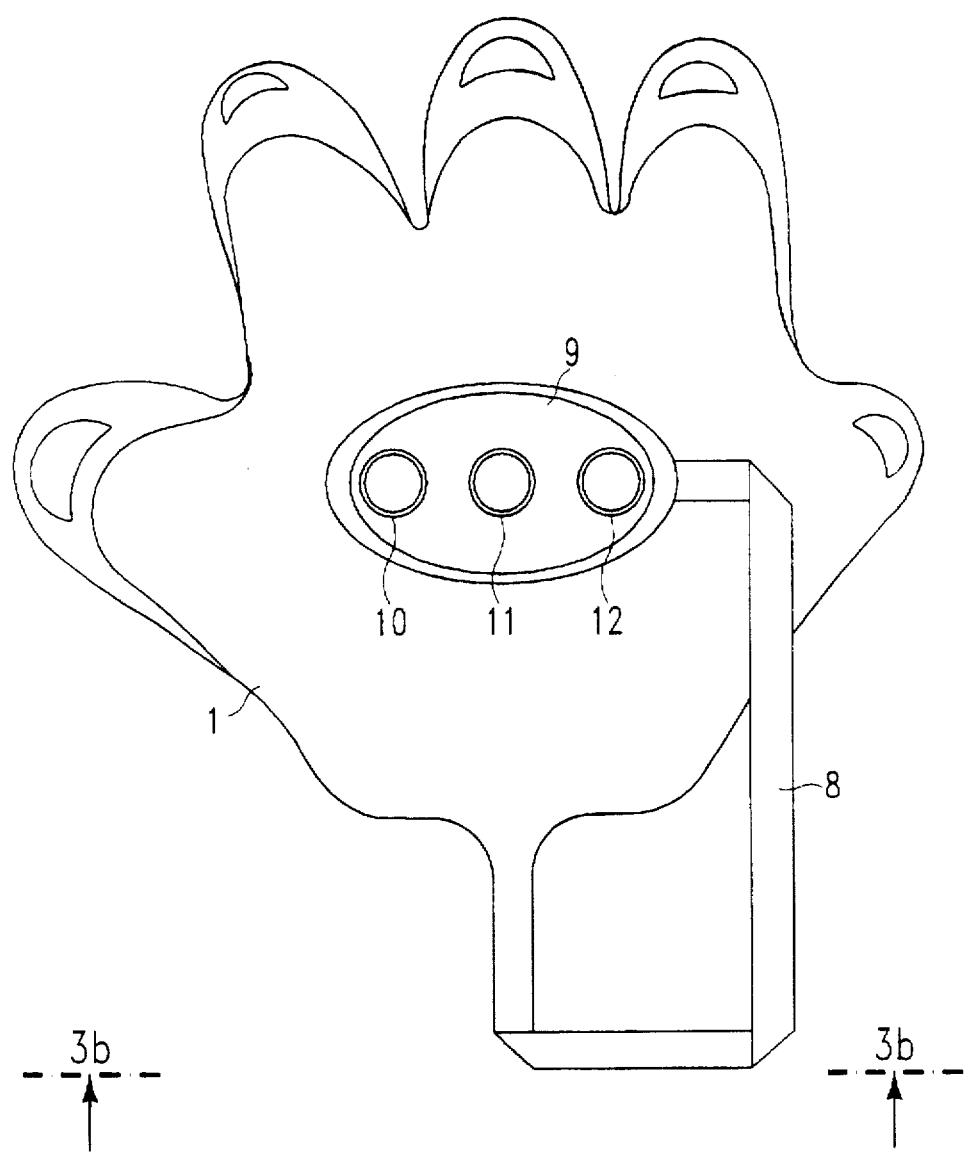
FIG.3(a) is a back view of the low-frequency electrotherapeutic device of the embodiment illustrated in FIG. 1, showing a controller attached to a base film sheet at a predetermined position.
Figure 3B:
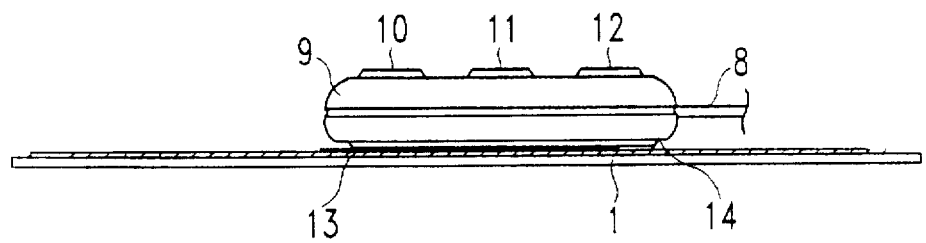
FIG.3(b) is a view as seen in the direction of arrow A in FIG. 3(a)

FIG. 2(a) is a back view of the low-frequency electrotherapeutic device illustrated in FIG. 1, showing a portion corresponding to the palm of the hand, FIG. 2(b) is a view as seen in the direction of arrow B in FIG. 1(a) and FIG. 2(c) is a side view of FIG. 2(b). Further, FIG. 3(a) is a back view of the low-frequency electrotherapeutic device illustrated in FIG. 1, showing the controller 9 held at a predetermined position on the base film sheet 1, and FIG. 3(b) is a view as seen in the direction of arrow A in FIG. 3(a).

As shown in FIG. 2(a)–2(c), a magic tape 13 is affixed to a nearly central position of the base film sheet 1, and a magic tape 14 is affixed to the back side of the controller 9, namely, the side opposite the side where the operating buttons 10, 11 and 12 are mounted. Therefore, as shown in FIGS. 3(a) and 3(b), when the low-frequency electrotherapeutic device of the embodiment illustrated in FIG. 1 to 3 is not in use, the controller 9 can be held onto the base film sheet 1 by joining the magic tape 13 on the controller 9 with the magic tape 14 on the base film sheet.

Figure 4:
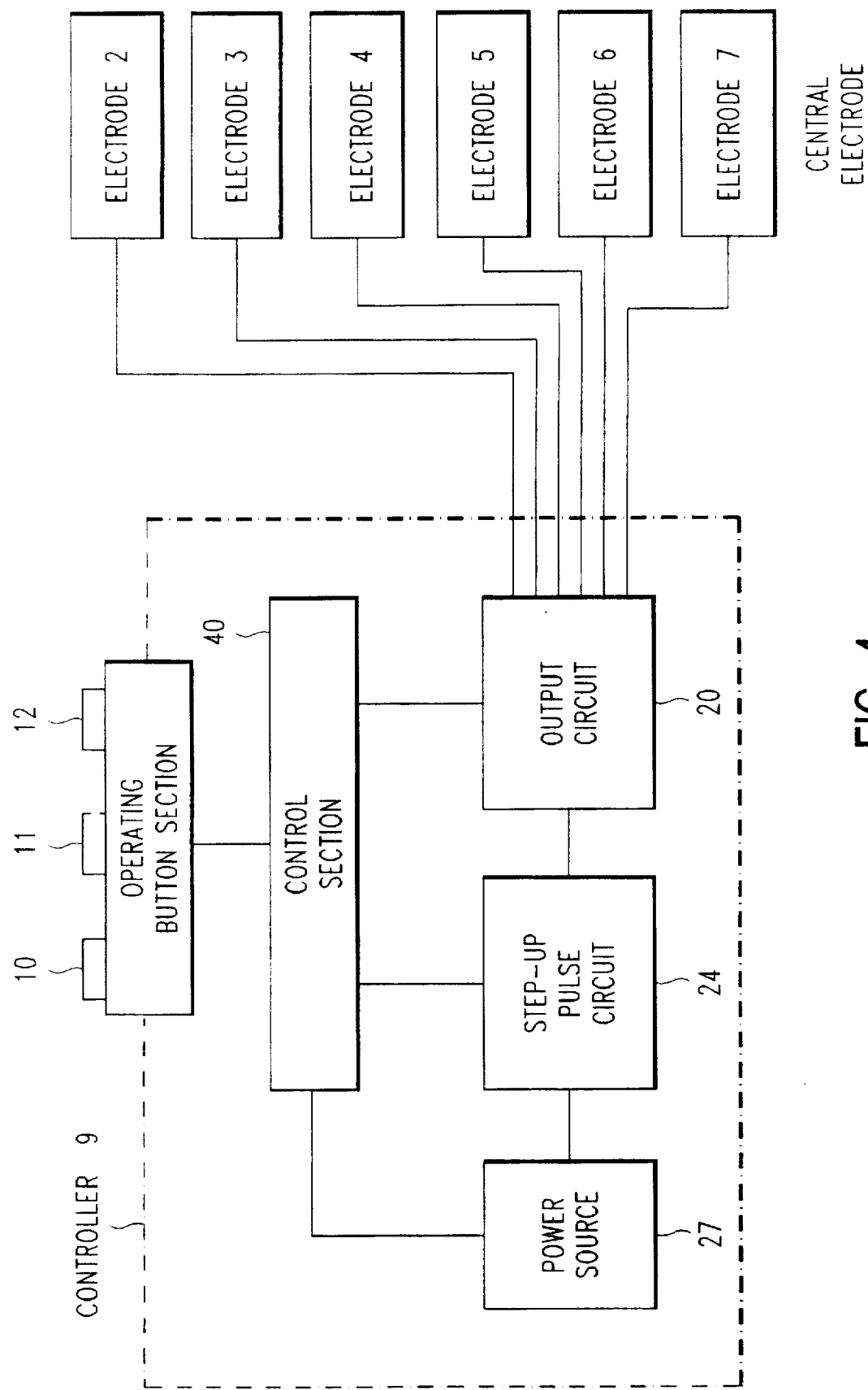
FIG.4 is a diagram showing a circuit configuration used in the low-frequency electrotherapeutic device of the embodiment illustrated in FIGS. 1 to 3.

FIG. 4 is a diagram showing a circuit configuration in the low-frequency electrotherapeutic device of the embodiment illustrated in FIGS. 1 to 3. The pendant type controller 9 is pendent outside through the pendant cable 8 which is integral with the base film sheet 1. In the interior space of the pendant type controller 9 are disposed a power source 27, a step-up pulse circuit 24, the operating switches 10, 11 and 12, an output circuit 26 including a scanning control function, and a control section (CPU) 40. As the power source 27 is used a button battery for example.

The oscillated signal which has been controlled in the control section (CPU) 40 is amplified to an amplitude several times as large as the original amplitude by means of the step-up pulse circuit 24. The step-up pulse circuit 24 then transmits the thus-amplified signal to the output circuit 26, which in turn converts the received signal into pulses having a predetermined width and a frequency, which are controlled by the control section (CPU) 40. The pulses are outputted to the electrodes.

According to the type of stimulation pattern, the output circuit 26 changes the waveform of pulses to be outputted in accordance with a command provided from the control section (CPU) 40 which has been programmed in advance. That is, the output circuit 26 controls the pulse width and amplitude of each pulse and outputs pulses having a group waveform in the shape of, for example, sine wave, square wave, or an exponential wave in which the magnitude increases and decreases exponentially. In accordance with the program stored in the control section (CPU), the output circuit 26 drives a scanning device included in the output circuit and performs an output control based on the combination of the electrodes.

The control section (CPU) 40 successively and selectively supplies output pulses from the output circuit 26 to a plurality of the electrodes 2, 3, 4, 5 and 6 and the central electrode 7. This control is executed by both CPU and program, the details of which will be omitted. As shown in FIGS. 1 and 2, the operating buttons of the pendant type controller 9 are mounted on the surface thereof. The three buttons 10, 11 and 12 are used to adjust the strength of output, select a stimulation pattern mode and make ON-OFF of the power source.

For example, when the operating button 10 is pushed, the power source turns ON. Upon further depression thereof, a signal is applied to the control section (CPU), so that the supply of the output pulses from the output circuit 26 to a plurality of the electrodes 2, 3, 4, 5, 6 and the central electrode 7 is increased.

When the operating button 12 is pushed, a signal is supplied to the control section (CPU), so that the supply of the output pulses from the output circuit 26 to a plurality of the electrodes 2, 3, 4, 5, 6 and the central electrode 7 is decreased. And upon further depression of the button 12, the power source turns OFF.

When the operating button 11 is pushed once or several times, a signal is fed to the control section (CPU), so that the group waveform of the output pulses supplied from the output circuit 26 to a plurality of the electrodes 2, 3, 4, 5 and 6 or in the central electrode 7 is changed in various ways.

In the low-frequency electrotherapeutic device illustrated in FIGS. 1 to 4 and described above, elements in the output circuit are selected in accordance with commands given from the control section (CPU) in the controller 9, whereby the electrodes 2, 3, 4 and 5 can be designated as different electrodes and the electrode 6 as an indifferent electrode, or likewise one of the electrodes 2, 3, 4 and 5 are designated as an indifferent electrode and the other electrodes as different electrodes. That is, each electrode can be designated as a different electrode or as an indifferent electrode. In the low-frequency electrotherapeutic device of this embodiment, the electrodes 2, 3, 4, 5 and the electrode 6 do not assume a fixed paired structure.

Moreover, in the low-frequency electrotherapeutic device of this embodiment, the supply of an electric current to the different electrodes 2, 3, 4, 5 and 6 can be changed by scanning whenever a predetermined period of time has elapsed, whereby the path of the stimulating current is changed whenever a predetermined period of time has elapsed. For example, the scanning is performed in the order of the different electrodes 2 - 3 - 4 - 5 - 6 - 2 - 3.

In the case where the electrodes 2, 3, 4, 5 and 6 are designated as indifferent electrodes, the path of the stimulating current can be changed by scanning those indifferent electrodes. Besides, since each electrode can be designated as a different electrode or an indifferent electrode, the path of the electric current flowing on the skin of a living body can be selected from various paths, the number of which corresponds to the number of paths connecting the electrodes, i.e., fifteen. As to the combination of electrodes, each electrode can be designated as one of two types of electrodes, i.e., a different electrode and an indifferent electrode, and there are six electrodes in all, each of which can be designated as one of the two types. Therefore, 26 types, i.e., 64 types, of electrode combinations are available. Out of the fifteen types of electric current paths or sixty-four types of electrode combinations, a desired type is selected in accordance with the program in the control section (CPU) incorporated in the controller 9 and it can be changed automatically at predetermined intervals.

Consequently, without frequent change of the affixed position of the base film sheet 1, the positions of the electrodes on the same sheet shift apparently, causing a change of stimulative positions as well.

Figure 5:
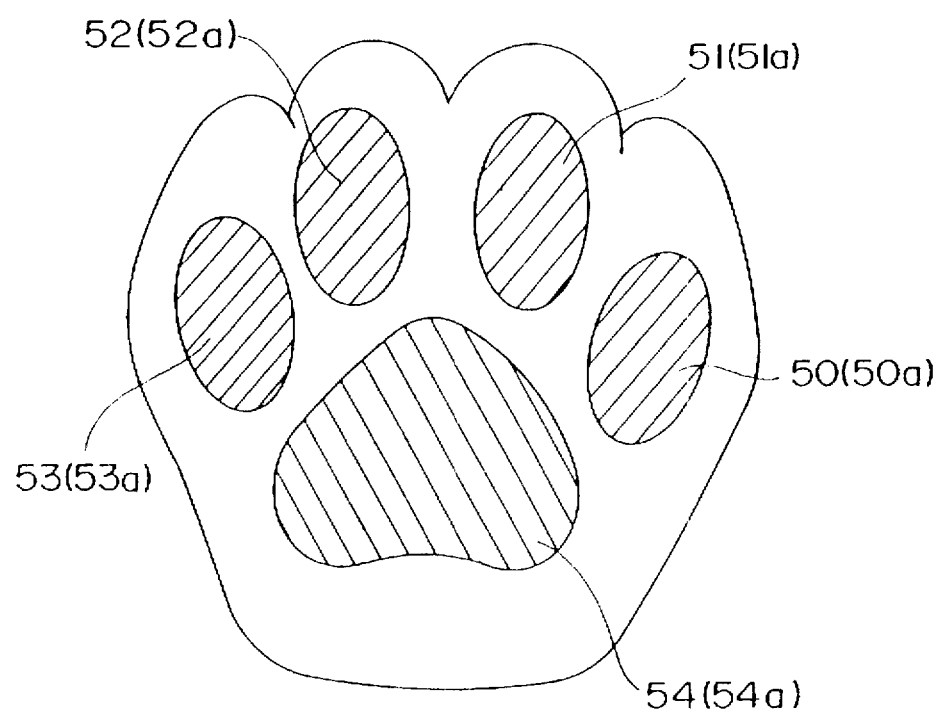
FIG. 5 is a surface view of a low-frequency electrotherapeutic device according to another embodiment of the present invention, showing a portion corresponding to the palm of the hand.

FIG. 5 is a surface view of a low-frequency electrotherapeutic device according to another embodiment of the present invention, showing a portion corresponding to the palm of the hand. The basic construction of this low-frequency electrotherapeutic device is the same as that of the low-frequency electrotherapeutic device of the previous embodiment described above. The low-frequency electrotherapeutic device of this embodiment is different from that of the previous embodiment in that the number of electrodes arranged on the base film sheet is five in all, comprising four fingertip electrodes and one palm electrode. Also in the low-frequency electrotherapeutic device of this embodiment, electrodes 50, 51, 52, 53 and 54 have medicinal adhesive pads 50a, 51a, 52a, 53a and 54a, respectively, and are arranged non-linearly on the surface a of a base film sheet 1. In other words, the electrodes 50, 52, 52, 53 and 54 are arranged on a curved line having a curvature smaller than infinity.

Further, also in the low-frequency electrotherapeutic device of the embodiment illustrated in FIG. 5, the electrodes 50, 51, 52 and 53 can be designated as different electrodes and the electrode 54 as an indifferent electrode by means of the control section (CPU) incorporated in the controller 9. Likewise, it is possible to designate one of the electrodes 50, 51, 52 and 53 as an indifferent electrode and the other electrodes as different electrodes. Thus, each electrode can be designated as a different electrode or as an indifferent electrode. A fixed paired structure of a different electrode and an indifferent electrode is not adopted like the previous embodiment.

In the low-frequency electrotherapeutic device of this embodiment, it is possible to change, through scanning, the supply of electric current to the electrodes 50, 51, 52 and 53 designated as different electrodes, whenever a predetermined period of time has elapsed. As a result, the stimulating current path can be changed whenever the predetermined period of time has elapsed. For example, scanning is performed in the order of different electrodes 50 - 51 - 52 - 53 - 50 - 51.

In the case where the different electrodes 50, 51, 52 and 53 are designated as indifferent electrodes, the stimulating current path can be changed by scanning those indifferent electrodes. In addition, since it is possible to set each electrode as a different electrode or as an indifferent electrode, the path of the electric current flowing on the skin of a living body can be changed in various paths, whose number corresponds to the number of paths connecting the electrodes, i.e., ten. As to the combination of electrodes, each electrode can be designated as one of two types of electrodes, i.e., a different electrode and an indifferent electrode, and there are five electrodes in all, each of which can be designated as one of the two types. Therefore, 25 types, i.e., 32 types, of electrode combinations are available. Out of the ten types of electric current paths or thirty-two types of electrode combinations, a desired type is selected in accordance with the program in the control section (CPU) incorporated in the controller 9 and it can be changed automatically at predetermined intervals.

Figure 11:
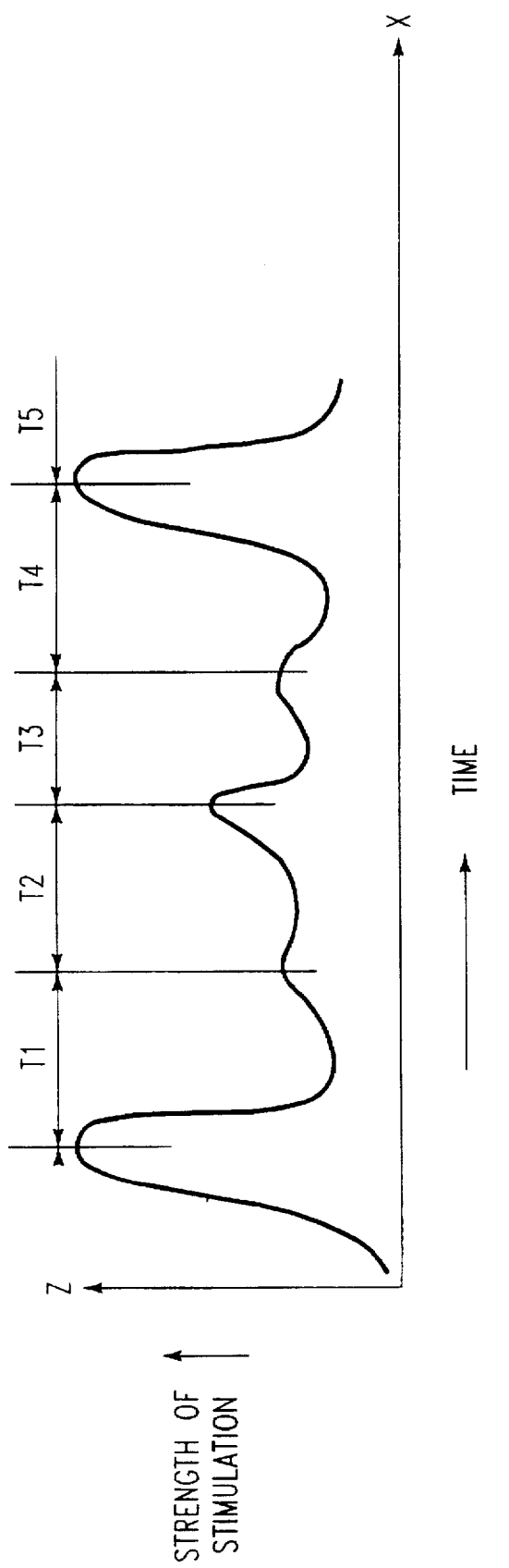
FIG.11 is an explanatory diagram showing changes in stimulation with elapse of time obtained when the 1/f fluctuation theory is applied to a conventional low-frequency electrotherapeutic device.
Figure 12:
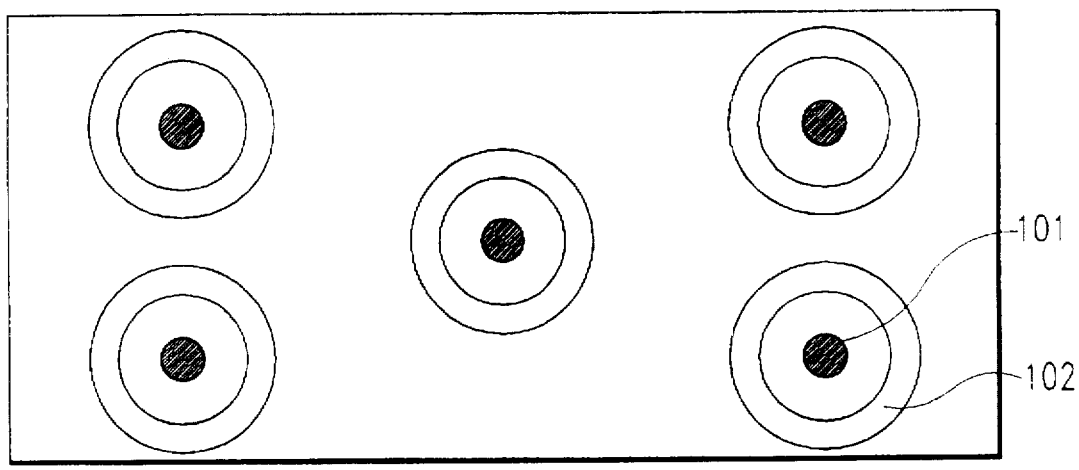
FIG. 12 is an explanatory diagram showing a conventional low-frequency electrotherapeutic device.
Figure 13:
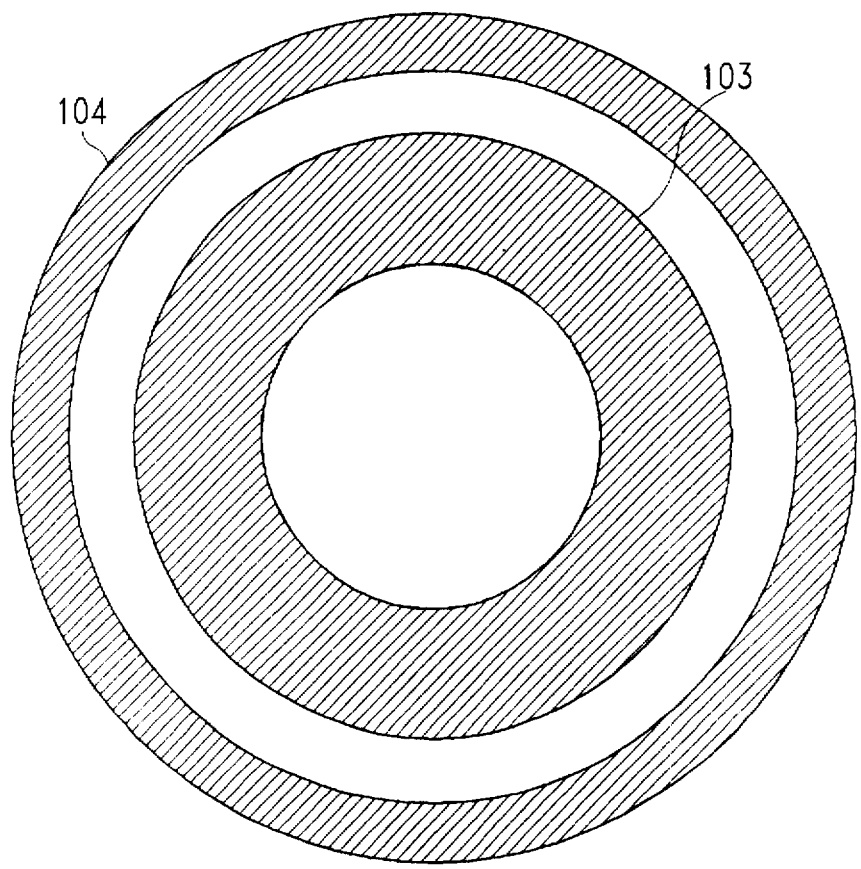
FIG. 13 is an explanatory diagram showing another conventional low-frequency electrotherapeutic device.
Figure 14:
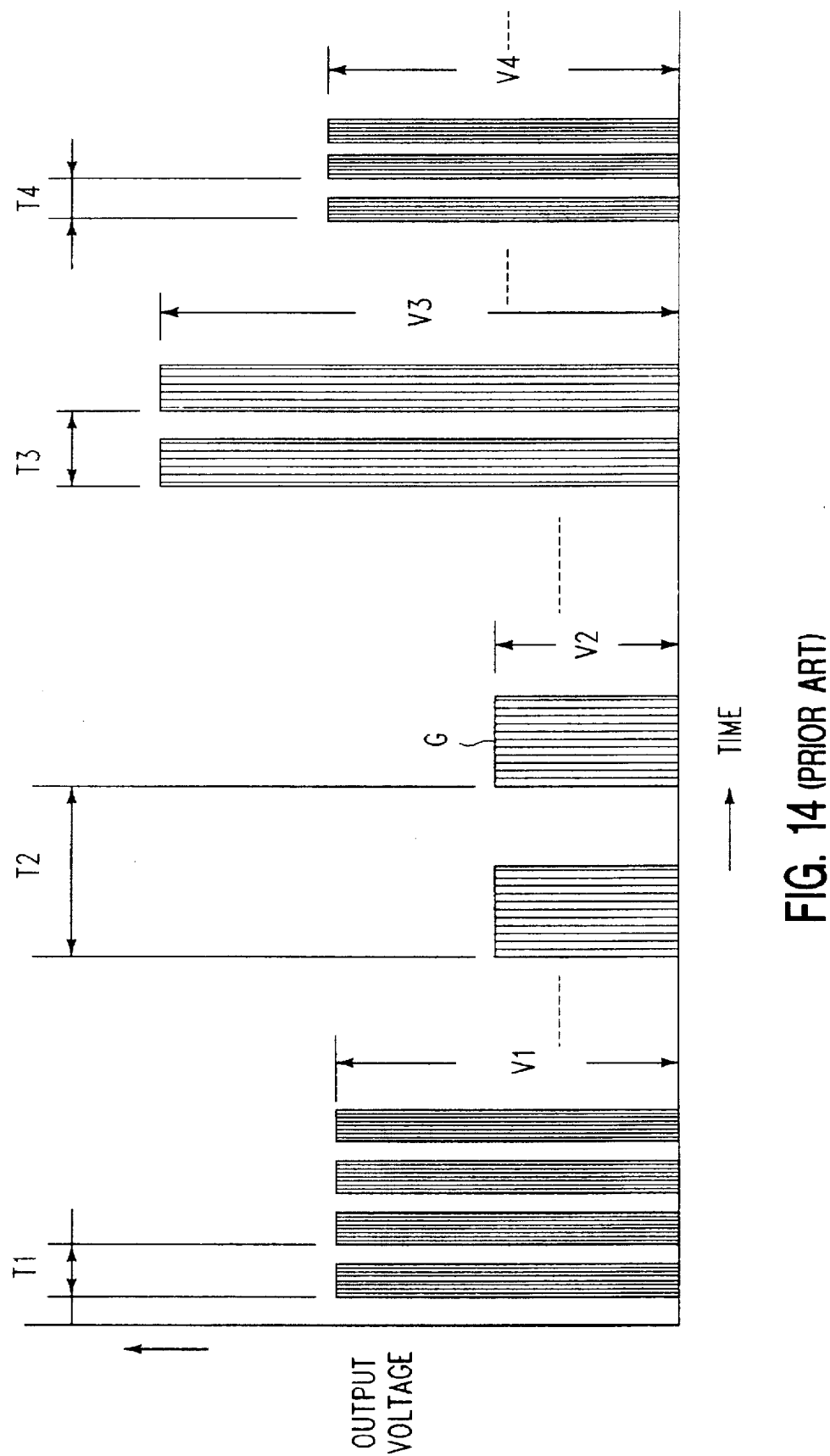
FIG. 14 is a diagram explaining a method of changing the type of stimulation automatically by changing the voltage waveform outputted from a different electrode.
Figure 15:
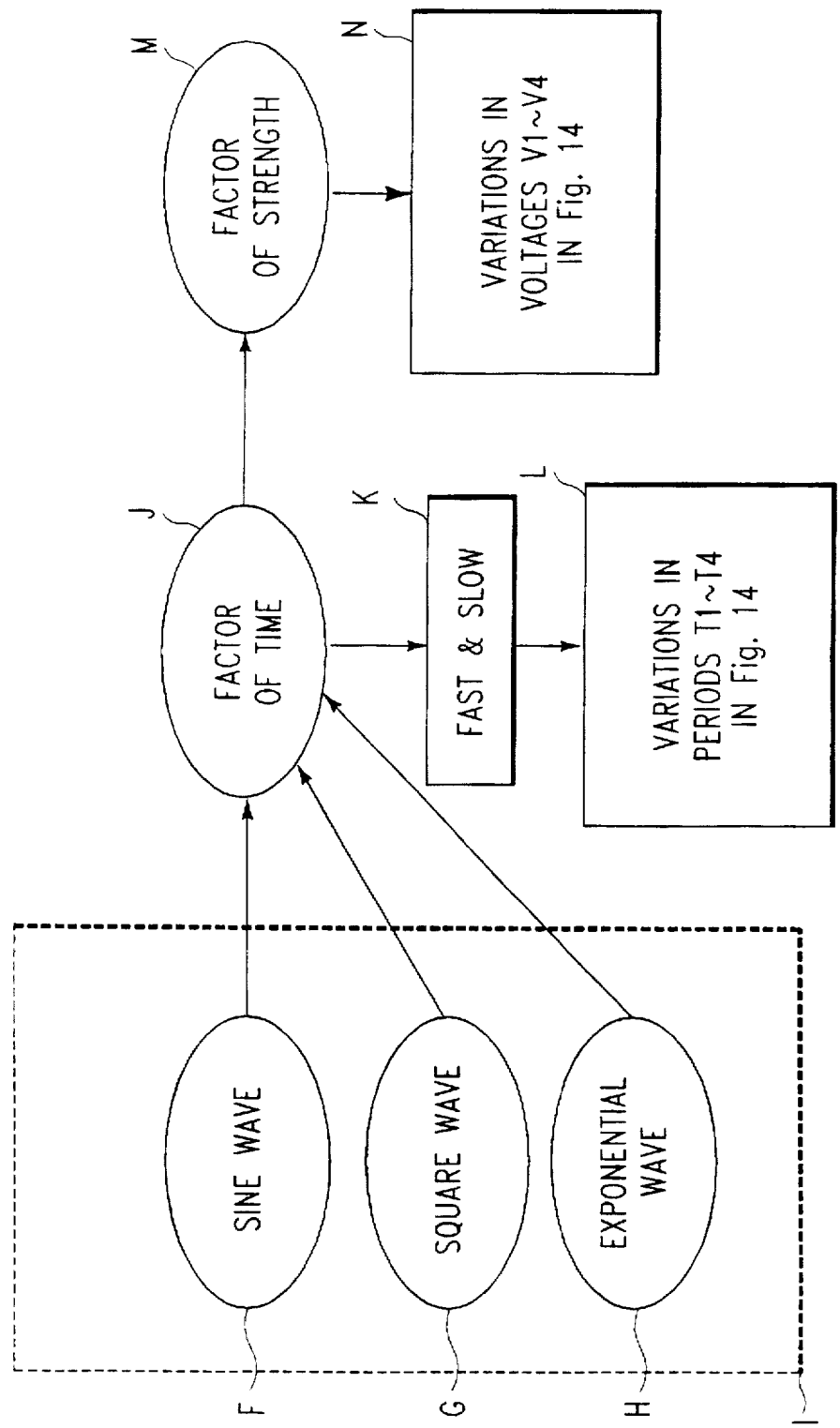
FIG. 15 is an explanatory diagram showing variation in the stimulation pattern of the conventional low-frequency electrotherapeutic device.

Next, a description will be given of an embodiment in which the change control method using a three-dimensional 1/f fluctuation according to the present invention is applied to the above-described low-frequency electrotherapeutic device. The T1 to T5 fluctuation periods shown in FIG.11 are synchronized with the timing of electric current supply to fingertip electrodes of the portions 1 to 5. As a result, pressing stimulations by the five fingers; that is, vertical stimulations (1/f fluctuation stimulations) each having a certain strength and rhythm are shifted simultaneously in the horizontal direction with a period of 1/f.

The following is an example of conducting the above three-dimensional 1/f fluctuation change control using actually-measured 1/f fluctuation waveforms.

Figure 6:
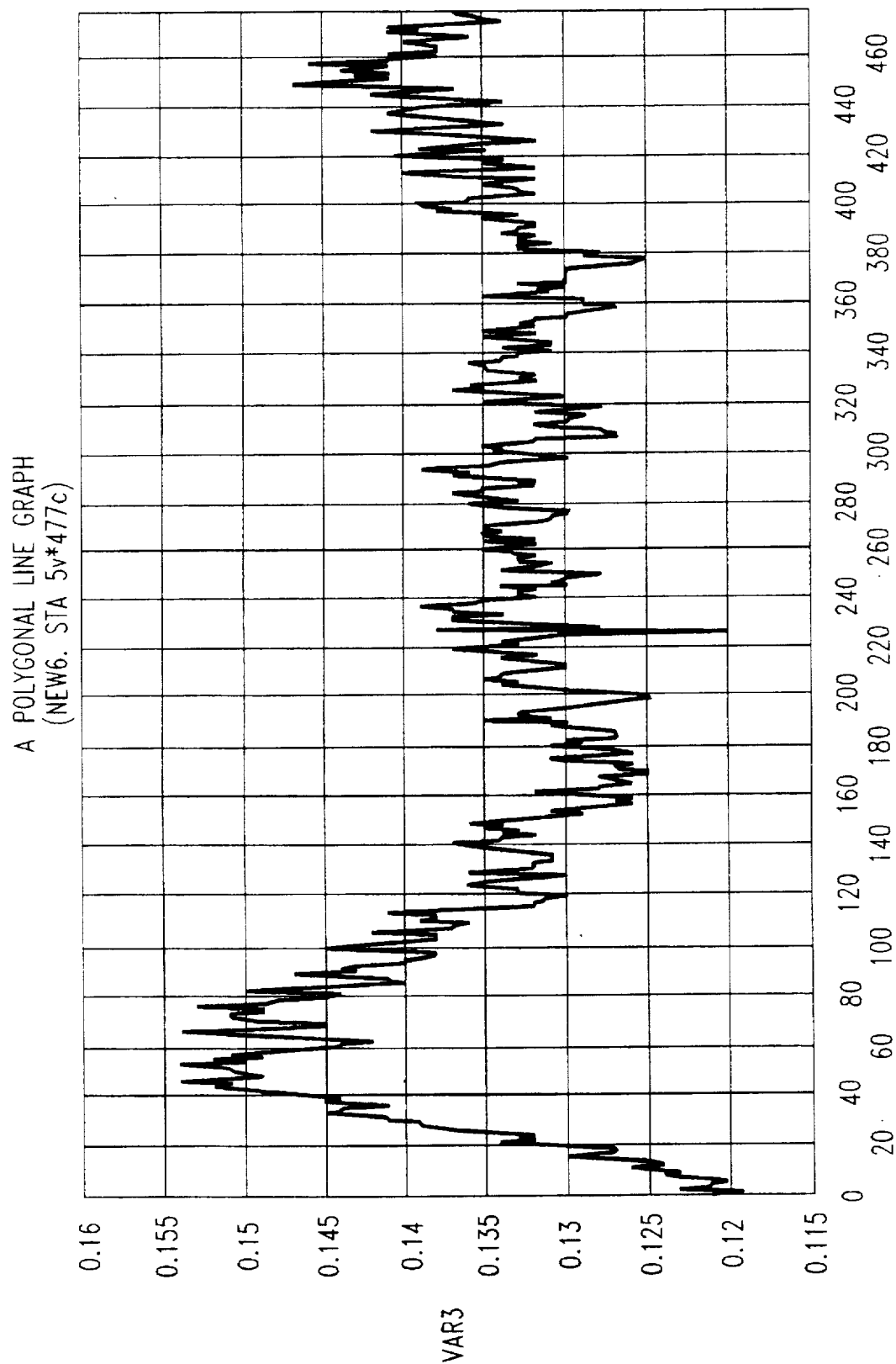
FIG.6 is a diagram showing electrocardiogram data obtained from a rat in a rest state.

The heart beat period in a living body in a rest state has 1/f fluctuation. On the basis of this fact, the inventor of the present invention have conducted an experiment. In this experiment, a small-sized telemetry transmitter was implanted into the living body of a rat (Wistar strain) for experimental use, and electrocardio data was obtained during a rest state of the rat. The measurement of the electrocardio data was conducted through use of wireless communication so as not to stress the rat. FIG.6 shows the electrocardio data. By spectral analysis from the electrocardio data shown in FIG. 6, data was examined in order to determine whether or not 1/f fluctuation occurred. As a result, there was obtained a generally rightward declining 1/f gradient line, as shown in FIG.7.

Figure 7:
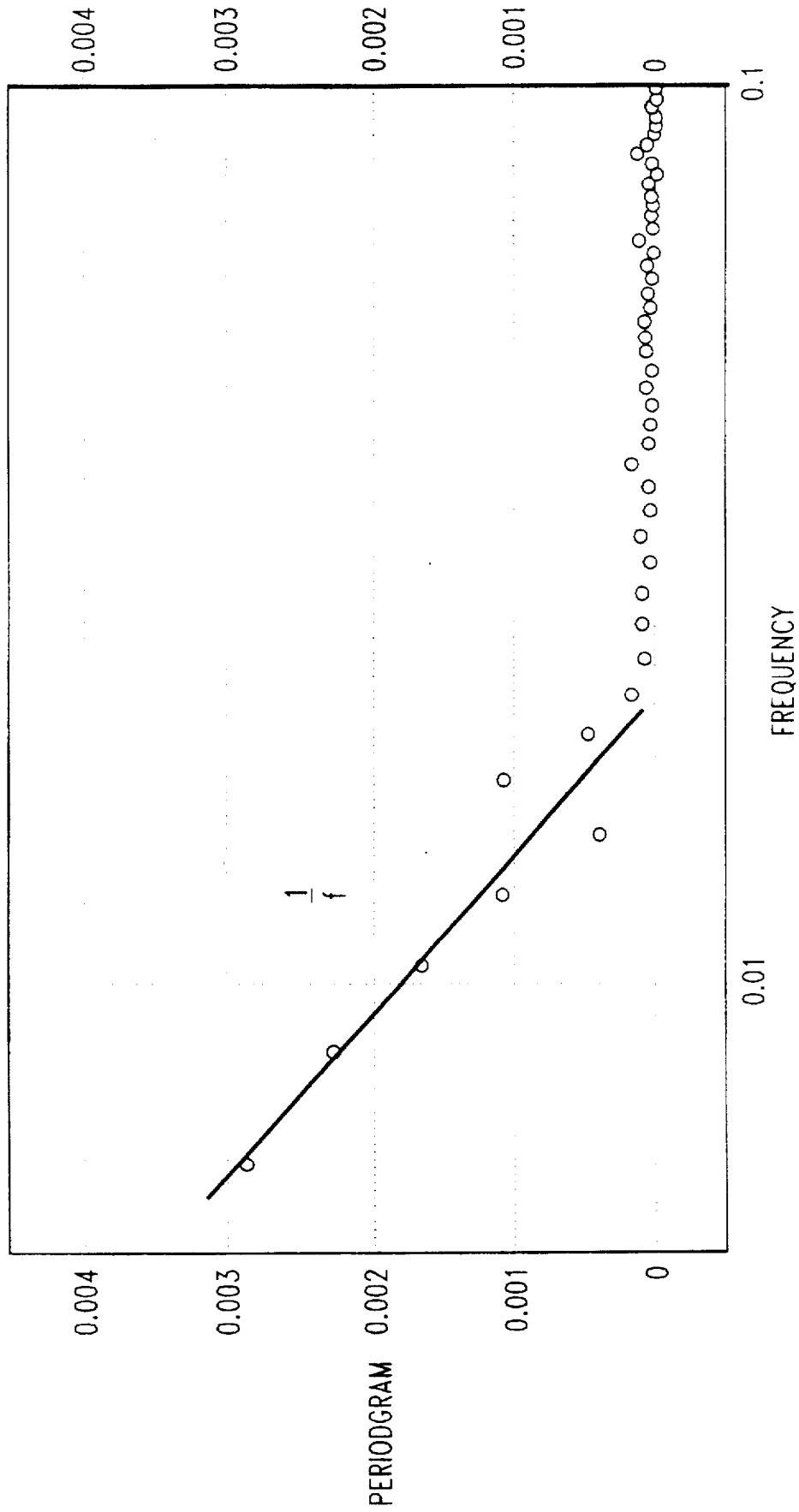
FIG.7 is a diagram obtained by spectral analysis of the electrocardiogram data.
Figure 8:
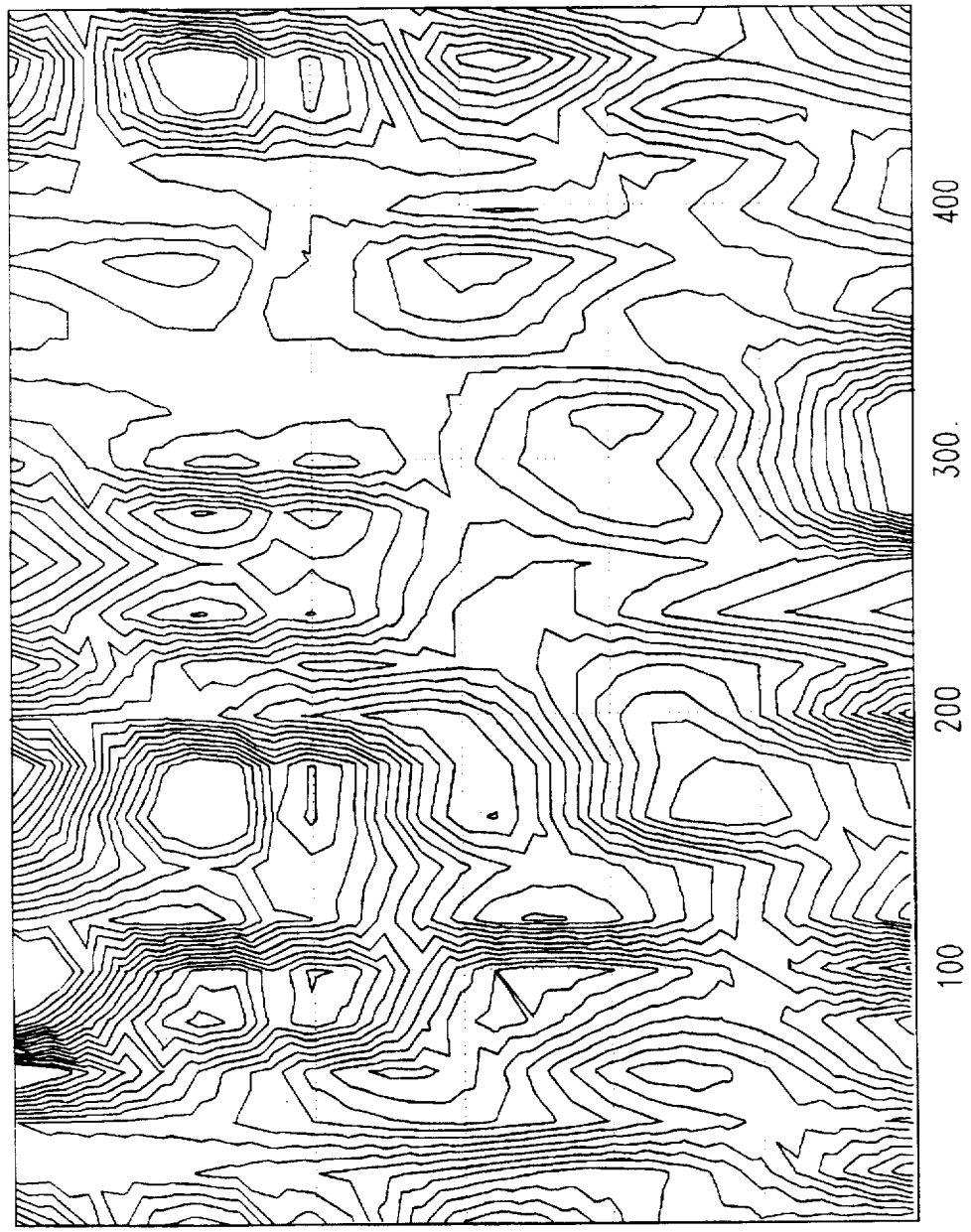
FIG.8 is a diagram obtained by extracting 1/f fluctuation from the data shown in FIG.7, determining the frequency and period density from the function by using Fourier analysis, determining 1/f fluctuation periods corresponding to the frequency while excluding of the shortest and the longest period so as to eliminate variations, and then applying the 1/f fluctuation periods to the Y-axis direct ion.

The diagram shown in FIG.8 was obtained by extracting 1/f fluctuation from FIG.7, determining the frequency and period density from the function through use of Fourier analysis, determining 1/f fluctuation periods corresponding to the frequency while excluding the shortest and the longest period in order to eliminate variations, and then applying the 1/f fluctuation periods to the Y-axis direction. The diagram shown in FIG. 8 is a time-series contour map which is obtained when a 1/f fluctuation is applied to each of the pressing forces VAR1 to VAR5 (the strengths of electrical stimulation strengths) provided by the respective fingers, and 1/f fluctuation periods are superposed in the horizontal direction of the pressing forces VAR1–VAR5. In this distribution diagram, the portions of dense contour lines indicate strong portions of electrical stimulation.

Figure 9:
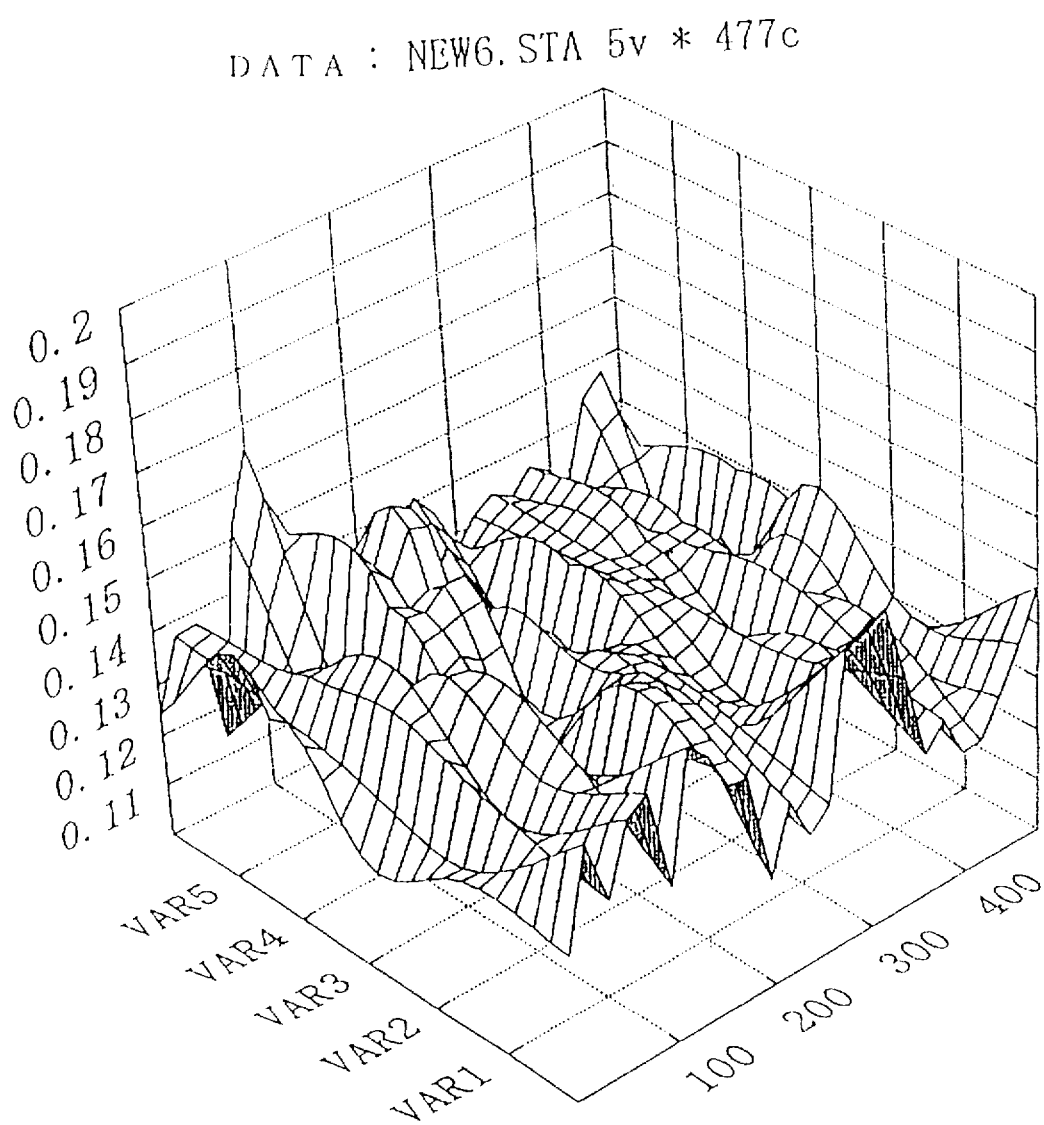
FIG.9 is a diagram obtained by expressing in three dimensions the time-series contour map shown in FIG. 8.

FIG. 9 is a diagram obtained by expressing the time-series contour map of FIG. 8 in three dimensions. In FIG. 9, peak positions indicate strong electrical stimulations. The undulation shown therein is in the form of three-dimensional 1/f fluctuation. FIG. 9 three-dimensionally shows a state of controlling the output voltages. In addition to the 1/f fluctuation in the X-Z direction involving changes in magnitude and period of the output voltage of a different electrode corresponding to a fingertip pressure as noted previously, an independent 1/f fluctuation in magnitude and period of the output voltage is also imparted to each of the remaining fingertips at the same time. Further, these fluctuations are shifted horizontally with 1/f fluctuation periods; that is, the fingertip different electrodes are scanned.

With the above stimulation pattern, changes are most closely resembling the changes in massage such as manual "kneading", "rubbing", and "tapping"; that is, changes which a human perceives as comfortable, can be simultaneously created on the five fingers. Thus, according to the low-frequency electrotherapeutic device of the above embodiment, stimulations based on the sense of human fingertips difficult to reproduce can be reproduced at any time which are in the form of new stimulations comprising a comfortable three-dimensional fluctuation.

Reference will be made below to various operation patterns in a medical treatment performed using the low-frequency electrotherapeutic device of the above-described embodiment.

(a) "Kneading" Operation Pattern

Figure 10:
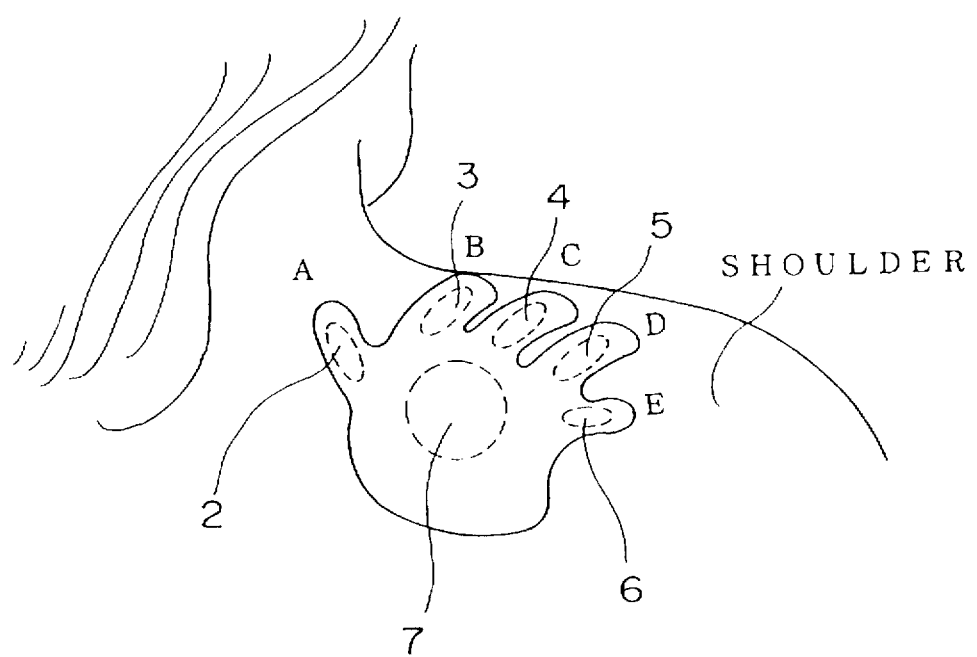
FIG.10 is a diagram showing the low-frequency electrotherapeutic device of the another embodiment as applied to the shoulder, which device is in the shape of a human hand.

FIG. 10 shows a state in which the low-frequency electrotherapeutic device of the embodiment illustrated in FIG. 1, having the shape of the human hand, is applied to the shoulder for example. Usually, when a person "kneads" the shoulder of another person, his or her hand assumes such a position as shown in FIG. 10.

In the "kneading" operation, a force is exerted on the portion A (thumb - electrode 2) and "kneading" operation is performed at the portions B (forefinger - electrode 3), C (middle finger - electrode 4) and D (third finger - electrode 5).

At this time, the portion A (thumb - electrode 2) functions as a fulcrum in the "kneading" operation and thereby permits execution of the "kneading" operation.

Further, when the person performing this operation grasps part of the shoulder and tries to exert a force on fingertips, the portion E (little finger - electrode 6) plays an important role. More particularly, unless the portion E (little finger - electrode 6) also functions as a fulcrum like the portion A (thumb - electrode 2), it is impossible to apply a sufficient force to the fingers of the portions B to D. In the case where a person "kneads" the shoulder of another person, a force is applied to fingertips at the balance mentioned above. The low-frequency electrotherapeutic device takes into account the above fact, and adopts a scanning method for the application of a pressing force, or electric stimulation, successively to the fingertips of the portions B (electrode 3)–C (electrode 4)–D (electrode 5) while applying a moderate pressing force, or electric stimulation to the portions A (thumb - electrode 2) and E (little finger - electrode 6). Thus, the low-frequency electrotherapeutic device can easily perform operations based on human engineering, involving sensing the pressing force at each fingertip of a massaging expert by means of a piezoelectric sensor and application of a voltage with electric stimulation scanning to the fingertips of the portions A to E on the basis of the data obtained by the piezoelectric sensor.

(b) "Rubbing" Operation Pattern

With the electric stimulation at a fixed limited position performed by the conventional low-frequency medical treatment devices, it is impossible to effect the "rubbing" operation. This is because the "rubbing" operation requires horizontal movements.

On the other hand, the low-frequency electrotherapeutic device according to the embodiment illustrated in FIG. 1 permits positional changes of stimulation because it adopts a free-running electrode system. Thus, the "rubbing" operation is the most favorite operation. More specifically, by scanning the electrodes 2, 3, 4, 5 and 6 in FIG. 1, the patient being treated by this low-frequency electrotherapeutic device can feel a natural "rubbing" massage through an electric stimulation.

In connection with the "rubbing" operation, the structure of the low-frequency electrotherapeutic device allows the "rubbing" operation to be performed in various patterns.

(c) "Tapping" Operation Pattern

The "tapping" operation in the conventional low-frequency electrotherapeutic devices is conducted at a single position because a different electrode and an indifferent electrode are fixed in a pair.

On the other hand, the low-frequency electrotherapeutic device of the present embodiment can adopt a method wherein the electrode 7 in FIG. 1 which electrode corresponds to the palm of the hand is designated as a different electrode of a large size, while the fingertip electrodes 2 to 6 are designated as indifferent electrodes, and those indifferent electrodes are scanned. According to this method, even when "tapping" stimulation is generated continuously in the electrode 7 designated as a different electrode, the stimulating current path is changed by scanning the fingertip electrodes 2 to 6 designated as indifferent electrodes, resulting in that it becomes possible to prevent the accumulation of an electric charge in a living body. Thus, it can be expected that the "tapping" effect obtained by using the low-frequency electrotherapeutic device will last long continuously without attenuation.

In connection with the above operation, it is possible to designate the electrode 7 as an indifferent electrode and the fingertip electrodes 2 to 6 as different electrodes and the position of stimulation provided by the electrodes 2 to 6 is changed whenever a predetermined period of time has elapsed. By the addition of this operation pattern, the "tapping" stimulation by the electrode 7 is followed by a soft "tapping" stimulation involving a positional shift around the electrode 7, whereby there is obtained a "tapping" sense which is more natural and closer to the human motion than the monotonous "tapping" stimulation at a limited position. This operation is effective also in preventing the tolerance of the nervous system.

Although the above operation patterns have been described with respect to the low-frequency electrotherapeutic device of the embodiment illustrated in FIG. 1, a low-frequency medical treatment using the same operation pattern can be performed by the low-frequency electrotherapeutic device of the embodiment illustrated in FIG. 5.

While solving the conventional problem that the change control is constant and repetitive, it is possible to control changes using a three-dimensional 1/f fluctuation to which a human can naturally and physiologically become accustomed. In the case where the changes to be controlled are changes in mechanical stimulation or changes in electrical stimulation, it becomes possible to apply the change control method according to the present invention to a mechanical or electrical massage extremely effectively.

While solving the conventional problem that the change control is constant and repetitive, it is possible to control changes using a three-dimensional 1/f fluctuation to which a human can naturally and physiologically become accustomed. In the case where the changes to be controlled are changes in mechanical stimulation or changes in electrical stimulation, the change control device according to the present invention can be constituted as an extremely effective mechanical or electrical massaging device.

The shift of stimulating positions in a low-frequency electrotherapeutic device, which is an example of the change control device using a three-dimensional 1/f fluctuation according to the present invention, is very effective in preventing an increase in the tolerance in neural response.

What is claimed is:

1. A change control method for controlling changes in stimulation to an object using a three-dimensional 1/f fluctuation, the method comprising the steps of:
   (a) causing stimulation changes based upon 1/f fluctuation periods in an X-Z plane of a X-Y-Z space;
   (b) causing stimulation changes based upon 1/f fluctuation periods in an X-Y plane of said space;
   (c) superposing said changes of steps (a) and (b) to form superposed changes; and
   (d) applying said superposed changes to the object.

2. A change control method according to claim 1, wherein the each of the steps of causing changes comprises the step of causing changes by mechanical motions.

3. A change control method according to claim 1, wherein the steps of causing changes comprise the step of causing changes in stimulation.

4. A change control method according to claim 1, wherein the steps of causing changes comprise the step of causing changes in electrical stimulation.

5. A change control method according to claim 1, wherein the steps of causing changes comprise the step of causing changes in artificially created topography.

6. A change control method according to claim 1, wherein the steps of causing changes comprise the step of causing changes in ups and downs found in a solid object.

7. A change control method according to claim 1, wherein the steps of causing changes comprise the step of causing changes in the flow of a fluid.

8. A change control method according to claim 1, wherein the steps of causing changes comprise the step of causing changes in pressure.

9. A recording medium read out by a computer which stores a change control method using a three-dimensional 1/f fluctuation, said medium being characterized in that changes based on 1/f fluctuation periods in the X-Z plane of a X-Y-Z space and changes based on 1/f fluctuation periods in the X-Y plane within said space are superposed on each other.

10. A change control device using a three-dimensional 1/f fluctuation, said change control device having a change control means for creating changes within a X-Y-Z space, wherein changes in an X-Z plane in the space and created based on 1/f fluctuation periods and changes in an X-Y plane in the space and created based on 1/f fluctuation periods are superposed on each other.

11. A change control device using a three-dimensional 1/f fluctuation according to claim 10, wherein said change control means comprises:

a step-up pulse circuit;
a control section (CPU) for controlling said step-up pulse circuit;
a power source for supplying electrical power to both said step-up pulse circuit and said control section (CPU);
an output circuit connected to said step-up pulse circuit and which is controlled by said control section (CPU); and
three or more electrodes connected to said output circuit and disposed in a X-Y-Z space wherein changes in an X-Z plane in the space and which are created by said electrodes based on 1/f fluctuation periods and changes in the X-Y plane which are created by said electrodes based on 1/f fluctuation periods are superposed on each other.

12. A change control device using a three-dimensional 1/f fluctuation according to claim 11, wherein said three or more electrodes comprise an arrangement oriented along a curved line whose curvature is smaller than infinity.

13. A change control device using a three-dimensional 1/f fluctuation according to claim 11, wherein a switching means is further provided to change an electric current path between a different electrode(s) and an indifferent electrode (s).

14. A change control device using a three-dimensional 1/f fluctuation according to claim 11, wherein a switching means is further provided to change an electric current path between a different electrode(s) and an indifferent electrode (s) and said output circuit provides a scanning control function to scan a plurality of electrodes serving as different electrodes or indifferent electrodes.

15. A change control device using a three-dimensional 1/f fluctuation according to claim 11, wherein three or more electrodes comprise an arrangement on a single sheet.

16. A change control device using a three-dimensional 1/f fluctuation, said change control device having a change control means for creating changes within a X-Y-Z space, said change control means comprises:

a step-up pulse circuit;
a control section (CPU) for controlling said step-up pulse circuit;
a power source for supplying electrical power to both said step-up pulse circuit and said control section (CPU);
an output circuit connected to said step-up pulse circuit and which is controlled by said control section (CPU); and
three or more electrodes connected to said output circuit and disposed in a X-Y-Z space;
wherein changes in an X-Z plane in said space which are created by said electrodes based on 1/f fluctuation periods and changes in an X-Y plane in the space which are created by said electrodes based on 1/f fluctuation periods are superposed on each other and said electrodes do not form a fixed pair of different and indifferent electrodes.

17. A change control device using a three-dimensional 1/f fluctuation, said change control device having a change control means for creating changes within a X-Y-Z space, said change control means comprises:

a step-up pulse circuit;
a control section (CPU) for controlling said step-up pulse circuit;
a power source for supplying electrical power to both said step-up pulse circuit and said control section (CPU);
output circuit connected to said step-up pulse circuit and which is controlled by said control section (CPU); and three or more electrodes connected to said output circuit and disposed in a X-Y-Z space;

wherein changes in an X-Z plane in the space and which are created by said electrodes based on 1/f fluctuation periods and changes in an X-Y plane in the space and which are created by said electrodes based on 1/f fluctuation periods are superposed on each other and a combination of different and indifferent electrodes is freely set.

18. A change control device using a three-dimensional 1/f fluctuation according to claim 17, wherein said three or more electrodes comprise a non-linear arrangement.

19. A change control device using a three-dimensional 1/f fluctuation, said change control device having a change control means for creating changes within an objection X-Y-Z space, said change control means comprises:

a step-up pulse circuit;

a control section (CPU) for controlling said step-up pulse circuit;

a power source for supplying electrical power to both said step-up pulse circuit and said control section (CPU);

an output circuit connected to said step-up pulse circuit and which is controlled by said control section (CPU); and three or more electrodes connected to said output circuit and disposed on the object in a X-Y-Z space, wherein changes in an X-Z plane in the space and which are created by said electrodes based on 1/f fluctuation periods and changes in an X-Y plane in the space and which are created by said electrodes based on 1/f fluctuation periods are superposed on each other and said electrodes are disposed at positions closely similar to positions of fingers and palm of the human hand.

* * * * *